United States Patent
Osawa

(10) Patent No.: US 11,258,990 B2
(45) Date of Patent: Feb. 22, 2022

(54) IMAGING SYSTEM AND IMAGING METHOD

(71) Applicant: OLYMPUS CORPORATION, Hachioji (JP)

(72) Inventor: Masato Osawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/190,778

(22) Filed: Mar. 3, 2021

(65) Prior Publication Data

US 2021/0195144 A1    Jun. 24, 2021

Related U.S. Application Data

(63) Continuation of application No. PCT/JP2019/000287, filed on Jan. 9, 2019.

(51) Int. Cl.
*H04N 7/18* (2006.01)
*A61B 1/00* (2006.01)

(52) U.S. Cl.
CPC .......... *H04N 7/183* (2013.01); *A61B 1/00009* (2013.01)

(58) Field of Classification Search
CPC ............................ H04N 7/183; A61B 1/00009
USPC .......................................................... 348/65
See application file for complete search history.

(56) References Cited

U.S. PATENT DOCUMENTS

| 2012/0066539 A1 | 3/2012 | Oikawa |
| 2017/0095141 A1* | 4/2017 | Tsutsui ............... A61B 1/00009 |
| 2018/0349595 A1* | 12/2018 | Sanandajifar ...... A61B 1/00013 |

FOREIGN PATENT DOCUMENTS

| EP | 3162275 A1 | 5/2017 |
| EP | 3285481 A1 | 2/2018 |
| JP | 2012-080513 A | 4/2012 |
| JP | 2012-245107 A | 12/2012 |
| JP | 6033523 B1 | 11/2016 |
| WO | 2016/208209 A1 | 12/2016 |
| WO | 2017/010114 A1 | 1/2017 |

OTHER PUBLICATIONS

International Search Report dated Apr. 9, 2019, issued in counterpart application No. PCT/JP2019/000287, w/English translation (3 pages).

* cited by examiner

*Primary Examiner* — Allen C Wong
(74) *Attorney, Agent, or Firm* — Westerman, Hattori, Daniels & Adrian, LLP

(57) ABSTRACT

In an imaging system according to an embodiment of the present invention, a camera unit is configured to transmit imaging data to an information-processing unit as a downlink packet. The camera unit is configured to hold predetermined data in the imaging data as a transmission key. The information-processing unit is configured to receive the downlink packet, recognize the predetermined data in the imaging data as the transmission key, and generate a reception key on the basis of the transmission key. The information-processing unit is configured to transmit an uplink packet including the reception key and a register-setting signal indicating an imaging condition to the camera unit. The camera unit is configured to write the register-setting signal received with the reception key in a register when the transmission key and the reception key meet a predetermined condition.

10 Claims, 7 Drawing Sheets

IMAGING SYSTEM AND IMAGING METHOD

The present application is a continuation application based on International Patent Application No. PCT/JP2019/000287 filed on Jan. 9, 2019, the content of which is incorporated herein by reference.

BACKGROUND OF THE INVENTION

Field of the Invention

The present invention relates to an imaging system and an imaging method.

Description of Related Art

An imaging system (endoscope system) that transmits and receives a test signal between a camera head (camera unit) and a main body (information-processing unit) of a processor on the basis of a test-start command from the information-processing unit and determines whether or not the state of communication by the test signal is good has been considered. For example, Japanese Patent No. 6033523 discloses an imaging system that executes register-setting by using control data (register-setting signal) when the state of communication is good.

SUMMARY OF THE INVENTION

According to a first aspect of the present invention, an imaging system includes a camera unit and an information-processing unit configured to communicate with each other in a wired or wireless manner. The camera unit includes an imager, a register, a collation circuit, a first transmission circuit, a holding circuit, and a writing circuit. The imager is configured to generate pixel data. An imaging condition of the imager is to be written in the register. The first transmission circuit is configured to transmit imaging data including the pixel data to the information-processing unit as a downlink packet. The holding circuit is configured to hold predetermined data in the imaging data as a transmission key. The information-processing unit includes a processing circuit and a second transmission circuit. The processing circuit is configured to receive the downlink packet, recognize the predetermined data in the imaging data as the transmission key, and generate a reception key on the basis of the transmission key. The second transmission circuit is configured to transmit an uplink packet including the reception key and a register-setting signal indicating the imaging condition to the camera unit. The writing circuit is configured to write the register-setting signal received with the reception key in the register when the collation circuit collates the transmission key held by the holding circuit with the reception key received from the information-processing unit and the transmission key and the reception key meet a predetermined condition.

According to a second aspect of the present invention, in the first aspect, the camera unit may include a first pad. The information-processing unit may include a second pad connected to the first pad by a signal transmission line. Communication of the downlink packet and the uplink packet may be performed by using the first pad and the second pad.

According to a third aspect of the present invention, in the first or second aspect, the camera unit may be configured to repeat a transmission phase, a reception phase, and an approval phase. The first transmission circuit may be configured to transmit the downlink packet to the information-processing unit in the transmission phase. The processing circuit may be configured to receive the uplink packet from the information-processing unit in the reception phase. The collation circuit may be configured to collate the transmission key with the reception key and determine whether or not the register-setting signal is to be written in the register in the approval phase. The first transmission circuit may be configured to transmit, in the transmission phase, information corresponding to a result of collating the transmission key with the reception key to the information-processing unit in the approval phase.

According to a fourth aspect of the present invention, in any one of the first to third aspects, the transmission key may be configured as information indicating the pixel data of a predetermined pixel.

According to a fifth aspect of the present invention, in the fourth aspect, the transmission key may include information indicating the uppermost bit of the pixel data of the predetermined pixel.

According to a sixth aspect of the present invention, in any one of the first to fifth aspects, the first transmission circuit may be configured to transmit the downlink packet including an error signal indicating an error position of the transmission key to the information-processing unit when the transmission key and the reception key do not meet the predetermined condition. The information-processing unit may be configured to execute an interpolation operation on a pixel corresponding to the error position.

According to a seventh aspect of the present invention, in any one of the first to third aspects, the imaging data may include the pixel data and service data for controlling start and completion of transmission of the pixel data. The transmission key may be part of the service data.

According to an eighth aspect of the present invention, in any one of the first to seventh aspects, the camera unit may further include an oscillator configured to generate an imager clock that is a reference of operation timings of the imager. The first transmission circuit may be configured to generate a signal by superimposing the imager clock on the imaging data and transmit the signal as the downlink packet to the information-processing unit. The information-processing unit may further include a system clock generator and a clock-data recovery circuit. The system clock generator is configured to generate a system clock in the information-processing unit. The clock-data recovery circuit is configured to reproduce the imager clock superimposed on the received downlink packet. The second transmission circuit may be configured to compare a frequency of the imager clock with a frequency of the system clock and transmit the register-setting signal for reducing deviation in frequency between the imager clock and the system clock as the uplink packet.

According to a ninth aspect of the present invention, in the eighth aspect, the oscillator may be configured as a voltage-controlled oscillator. The frequency of the imager clock may be changeable in accordance with a voltage applied to the voltage-controlled oscillator. The camera unit may further include a digital-to-analog convertor configured to supply a voltage to the voltage-controlled oscillator on the basis of a frequency that has been set in the register.

According to a tenth aspect of the present invention, an imaging method in an imaging system including a camera unit and an information-processing unit is provided. The method includes a first step, a second step, a third step, a fourth step, and a fifth step. The camera unit and the information-processing unit are configured to communicate with each other in a wired or wireless manner. The camera unit includes an imager configured to generate pixel data, a register in which an imaging condition of the imager is to be written, a collation circuit, a first transmission circuit, a holding circuit, and a writing circuit. The information-processing unit includes a processing circuit and a second transmission circuit. The first transmission circuit transmits imaging data including the pixel data to the information-processing unit as a downlink packet in the first step. The holding circuit holds predetermined data in the imaging data as a transmission key in the second step. The processing circuit receives the downlink packet, recognizes the predetermined data in the imaging data as the transmission key, and generates a reception key on the basis of the transmission key in the third step. The second transmission circuit transmits an uplink packet including the reception key and a register-setting signal indicating the imaging condition to the camera unit in the fourth step. The writing circuit writes the register-setting signal received with the reception key in the register in the fifth step when the collation circuit collates the transmission key held by the holding circuit with the reception key received from the information-processing unit and the transmission key and the reception key meet a predetermined condition.

DETAILED DESCRIPTION OF THE INVENTION

Figure 1:
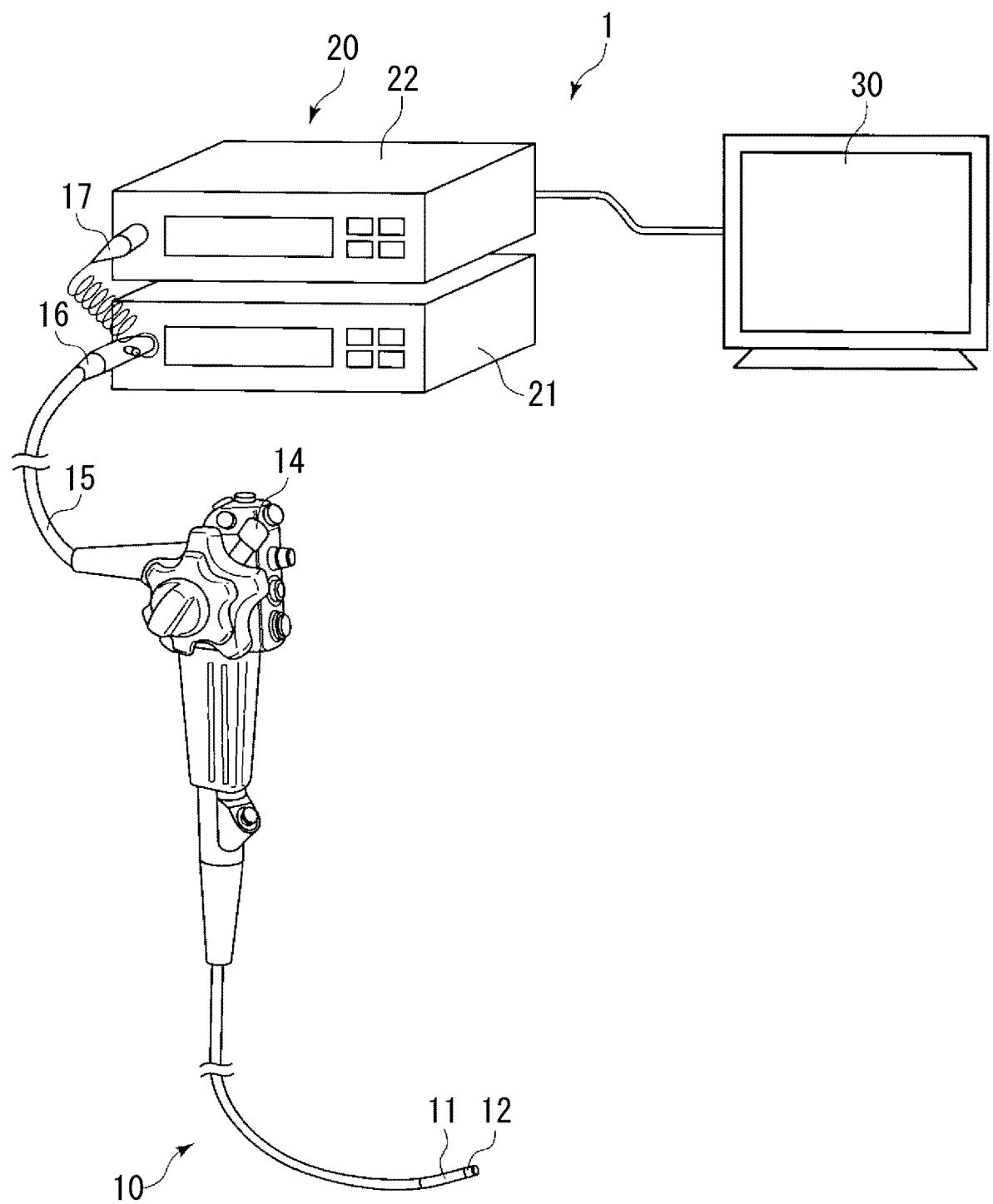
FIG. 1 is a diagram showing a schematic configuration of an endoscope system including an endoscope according to an embodiment of the present invention.

Hereinafter, embodiments of the present invention will be described with reference to the drawings. FIG. 1 is a diagram showing a schematic configuration of an endoscope system including an endoscope according to an embodiment of the present invention. The endoscope system (imaging system 1) shown in FIG. 1 includes a scope 10, a controller 20, and a monitor 30. The scope 10 transmits imaging data of the inside of a body of a subject to an image processor 22 of the controller 20. The image processor 22 processes the imaging data transmitted from the scope 10. The monitor 30 displays a picture on the basis of the imaging data processed by the controller 20.

The scope 10 functioning as an endoscope in the embodiment includes an insertion unit 11, an operation unit 14, a cable 15, a connector 16, and a connector 17.

The insertion unit 11 is a portion to be inserted into the inside of the body of the subject. A camera unit 2 including an imager 201 is provided inside the distal end of the insertion unit 11. The imager 201 is a CMOS sensor or a CCD sensor, images the inside of the body of the subject, and generates imaging data related to the subject. The configuration of the camera unit 2 will be described in detail later. In addition, the insertion unit 11 is configured to emit illumination light from the distal end.

The insertion unit 11 is configured so as to include a portion designed to curve by receiving an operation of an operation knob of the operation unit 14 by an operator such as a doctor and include a portion that passively curves by external force regardless of the operation of the operation unit 14.

The operation unit 14 connects the insertion unit 11 and the cable 15 together. The operation unit 14 includes an RL knob for performing an operation of curving the insertion unit 11 in the right and left directions and a UD knob for performing an operation of curving the insertion unit 11 in the up and down directions. In addition, the operation unit 14 includes various switches.

A light guide has been formed inside the insertion unit 11, the operation unit 14, and the cable 15. This light guide is connected to a light source device 21 of the controller 20 by the connector 16 provided in the base end of the cable 15. In addition, various signal lines including a video signal line and the like as a transmission line for transmitting the imaging data have been formed inside the insertion unit 11, the operation unit 14, and the cable 15. These signal lines, in other words, signal lines including a differential-signal transmission line described later are connected to the image processor 22 of the controller 20 by the connector 17 connected to the connector 16. Furthermore, channels are provided for the purpose of passing from the operation unit 14 to the insertion unit 11. The channels are provided so that various kinds of treatment tools including an ultrasonic coagulation-and-incision apparatus such as an ultrasonic scalpel, a high-frequency current generator such as an electric scalpel, and the like are inserted to the distal end of the insertion unit 11. With these channels provided, observation using an endoscope and treatment using treatment tools can be simultaneously performed.

All the components of an information-processing unit 3 of the embodiment, including an imaging-signal-processing unit 300 and the like, may be included in the image processor 22. Details of the information-processing unit 3 will be described later. Some of the components of the information-processing unit 3 such as a receiver 301 and an output driver 306 may be included in a portion, for example, the connector 16 and the connector 17 different from the image processor 22.

The light source device 21 includes a light source such as a white LED and emits illumination light. The illumination light emitted from the light source device 21 is delivered to the distal end of the insertion unit 11 by the light guide and is emitted from the distal end of the insertion unit 11. In this way, the inside of the subject is illuminated.

The information-processing unit 3 as an external signal-processing apparatus of an imaging device 12 (camera unit 2 described later) processes imaging data acquired in the imaging device 12 of the insertion unit 11. This processing includes processing of converting imaging data on which gradation correction or the like has been performed into a format that the monitor 30 is able to display.

The monitor 30 (display 4 shown in FIG. 2) is, for example, a liquid crystal monitor. The monitor 30 displays various kinds of information and pictures on the basis of the imaging data processed by the information-processing unit 3.

First Embodiment

Figure 2:
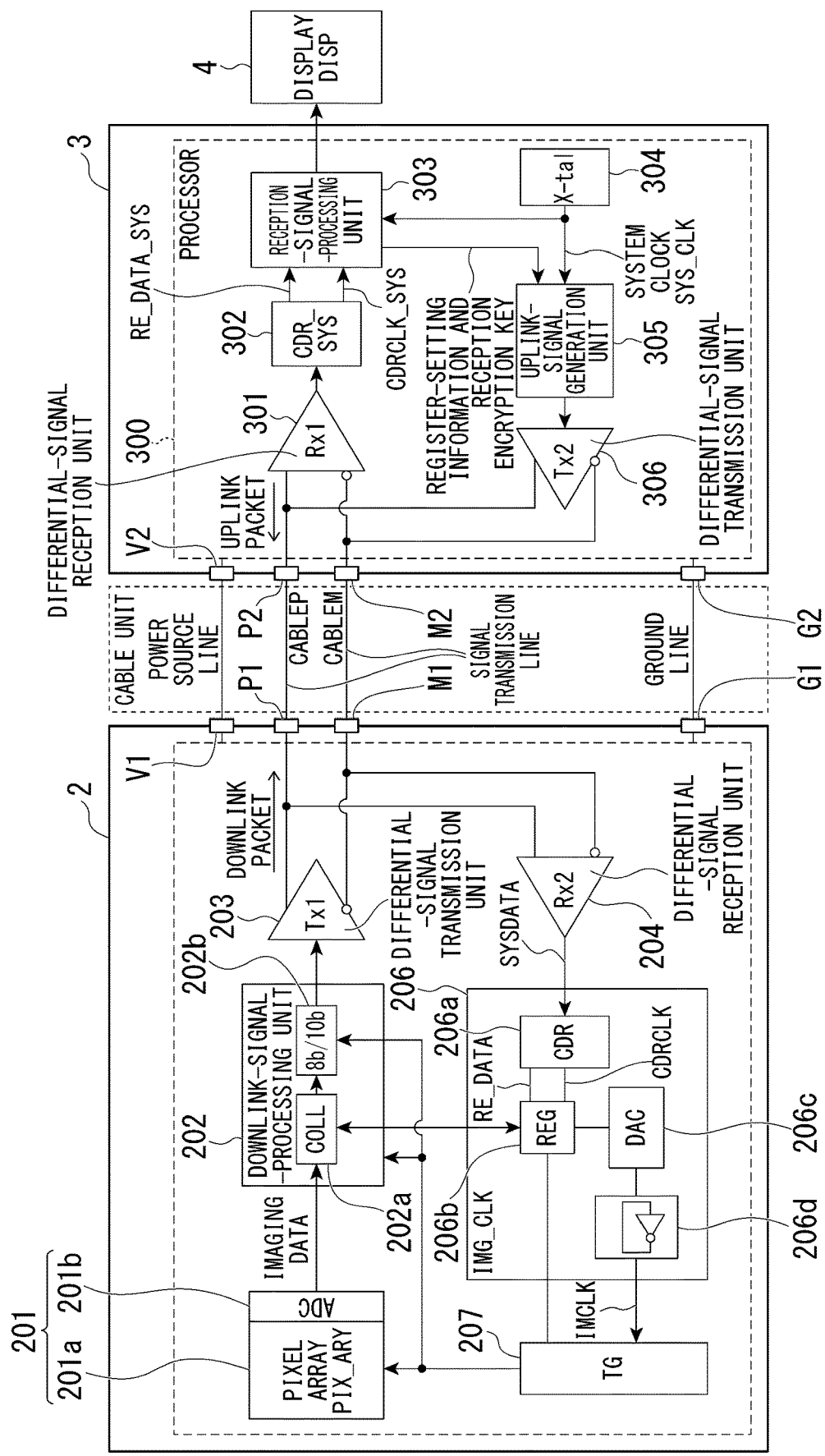
FIG. 2 is a block diagram showing an example of a configuration of an imaging system according to the embodiment of the present invention.

FIG. 2 is a block diagram showing an example of a configuration of an imaging system according to a first embodiment of the present invention.

The imaging system 1 is configured as an imaging system in which the camera unit 2 and the information-processing unit 3 are able to perform two-way communication in a wired or wireless manner.

In the imaging system 1, the camera unit 2 includes a pad P1 and a pad M1 (first pad). The pad P1 executes transmission of a downlink packet and the pad M1 executes reception of an uplink packet. The information-processing unit 3 includes a pad P2 and a pad M2 (second pad). The pad P2 executes transmission of the uplink packet and the pad M2 executes reception of the downlink packet. The pad P1 and the pad P2 are connected to each other by a signal transmission line (cable CABLEP), and the pad M1 and the pad M2 are connected to each other by a signal transmission line (cable CABLEM). Transmission and reception of the downlink packet and the uplink packet are executed by using the first pad and the second pad.

<Configuration of Camera Unit 2>

The camera unit 2 shown in FIG. 2 includes the imager 201, a downlink-signal-processing unit 202, an output driver 203, a receiver 204, an imager-clock generation unit 206 and a timing generator 207. The output driver 203 is shown as a differential-signal transmission unit Tx1 (first transmission circuit). Hereinafter, the differential-signal transmission unit Tx1 is called an output driver Tx1. The receiver 204 is shown as a differential-signal reception unit Rx2. Hereinafter, the differential-signal reception unit Rx2 is called a receiver Rx2. The timing generator 207 is shown as TG in FIG. 2.

The imager 201 includes a PIX unit 201a shown as a pixel array PIX_ARY and a signal-processing circuit 201b (COL_ADC).

The PIX unit 201a includes a plurality of pixels P. In other words, in FIG. 2, unit pixels P, each including a photoelectric conversion element, are two-dimensionally arranged in a matrix shape and constitute the PIX unit 201a including a plurality of pixel arrays. Hereinafter, the unit pixel P is simply called a pixel.

In addition, the signal-processing circuit 201b is a so-called column analog-to-digital converter (ADC) that converts an analog signal output from a pixel P into a digital signal while suppressing fixed-pattern noise of the pixel by using analog-to-digital (AD) conversion circuits that perform processing in parallel for each column of the pixels P of the PIX unit 201a. The digital signal generated and output by the signal-processing circuit 201b is shown as imaging data in FIG. 2. The imaging data are shown as imaging data including digital signals (pixel data) of the pixels P. In addition, predetermined partial data are included as a transmission encryption key in the imaging data. Hereinafter, the transmission encryption key is called a transmission key.

The downlink-signal-processing unit 202 includes a collation circuit 202a and a packet-combining unit 202b. The collation circuit 202a is shown as COLL in FIG. 2. The imaging data are shown as 8b/10b (bits) in FIG. 2.

The collation circuit 202a collates a transmission key consisting of the predetermined partial data in the imaging data with a reception encryption key generated on the basis of the transmission key by the information-processing unit 3. Hereinafter, the reception encryption key is called a reception key. When a collation result indicating that the transmission key and the reception key meet a predetermined condition is obtained, the collation circuit 202a (writing circuit) writes a register-setting signal received with the reception key in a register unit 206b in the imager-clock generation unit 206. The register-setting signal is a setting signal indicating an imaging condition of the imager 201. Hereinafter, the imager-clock generation unit 206 is called an imager-clock generation unit IMG_CLK. The collation circuit 202a may output the collation result to a writing circuit in the camera unit 2 and the writing circuit may write the register-setting signal received with the reception key in the register unit 206b.

The packet-combining unit 202b superimposes an imager clock IMCLK generated by a voltage-controlled oscillator 206d in the imager-clock generation unit IMG_CLK on the imaging data including the transmission key, thus generating a downlink packet.

The output driver Tx1 converts the downlink packet into a pair of differential signals and outputs the differential signals from the pad P1 and the pad M1 to a pair of signal transmission lines (two cables CABLEP and CABLEM). The pair of differential signals are output to the receiver 301 of the information-processing unit 3 through the pad P2 and the pad M2 of the information-processing unit 3 connected to the signal transmission lines.

The receiver Rx2 receives an uplink packet (the reception key and the register-setting signal) transmitted by the information-processing unit 3 and outputs reception data SYS-DATA as an output signal to the imager-clock generation unit IMG_CLK.

Next, a detailed configuration and operation of the imager-clock generation unit IMG_CLK included in the camera unit 2 shown in FIG. 2 will be described with reference to FIG. 3 and FIG. 4.

Figure 3:
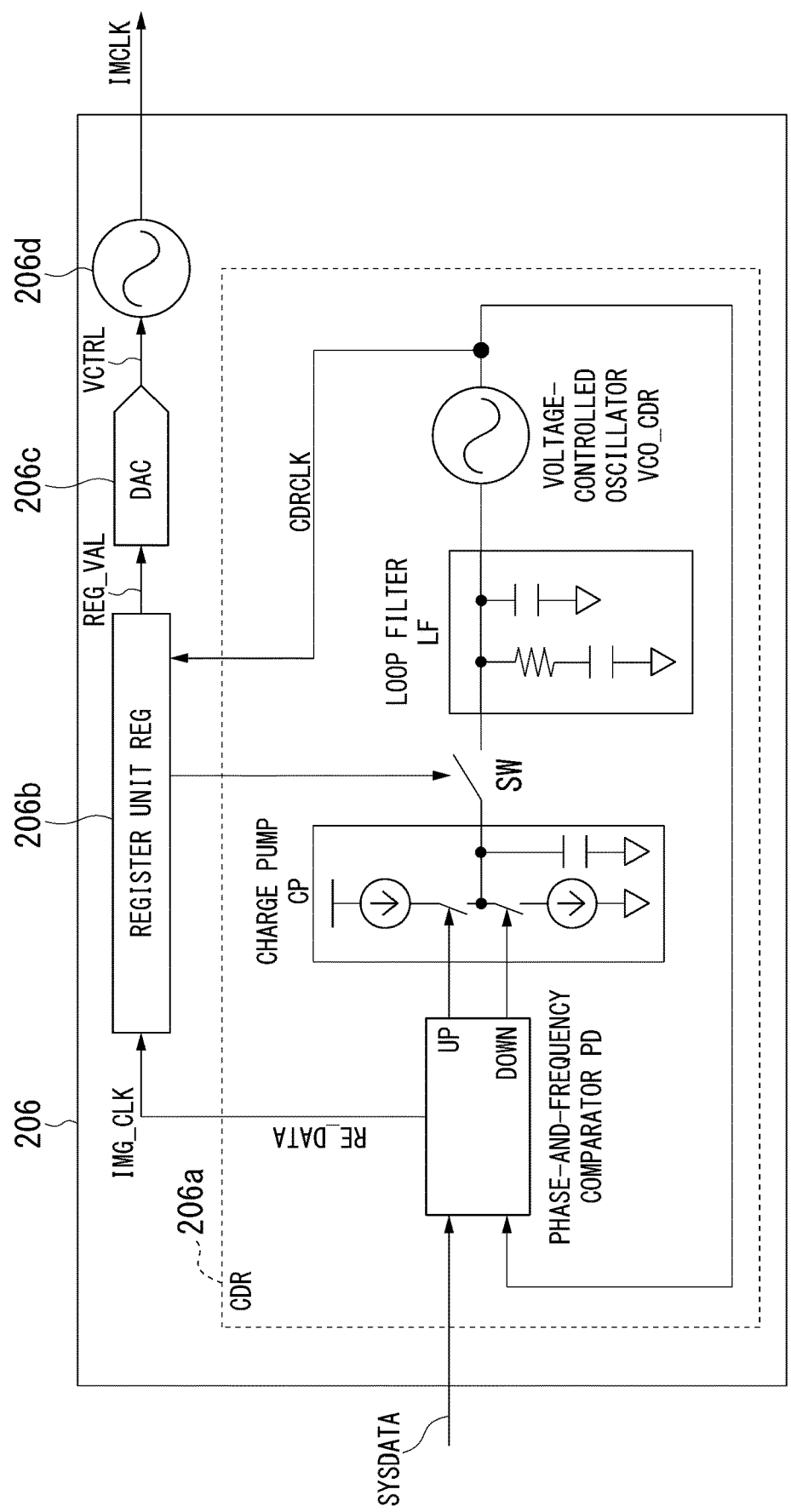
FIG. 3 is a diagram showing a configuration of an imager-clock generation unit IMG_CLK shown in FIG. 2.

FIG. 3 is a diagram showing a configuration of the imager-clock generation unit IMG_CLK shown in FIG. 2. In addition, FIG. 4 is a timing chart showing a logical state of a major node of the imager-clock generation unit IMG_CLK shown in FIG. 2.

The imager-clock generation unit IMG_CLK includes a clock-data recovery unit 206a, the register unit 206b, a digital-to-analog convertor 206c, and the voltage-controlled oscillator 206d. Hereinafter, the voltage-controlled oscillator 206d is called a voltage-controlled oscillator VCO_IMCLK.

The clock-data recovery unit 206a is shown as CDR in FIG. 3. Hereinafter, the clock-data recovery unit 206a is called a clock-data recovery unit CDR. In addition, the register unit 206b is shown as REG in FIG. 3. Hereinafter, the register unit 206b is called a register unit REG. In addition, the digital-to-analog convertor 206c is shown as DAC in FIG. 3. Hereinafter, the digital-to-analog convertor 206c is called a digital-to-analog convertor DAC.

The voltage-controlled oscillator VCO_IMCLK outputs the imager clock IMCLK to the timing generator TG. The imager clock IMCLK oscillates at a frequency in accordance with an input control voltage VCTRL. The timing generator TG is shown as the tuning generator 207 in FIG. 2. Thus, the camera unit 2 performs an operation synchronized with the imager clock IMCLK.

The digital-to-analog convertor DAC outputs the control voltage VCTRL (analog signal) in accordance with an input register value REG VAL (digital signal).

Register data RE_DATA are input to the register unit REG in synchronization with a CDR clock CDRCLK input from the clock-data recovery unit CDR and the value of the register data RE_DATA is held in the register unit REG.

The reception data SYSDATA are input to the imager-clock generation unit IMG_CLK. The reception data SYSDATA include a clock-recovery symbol for each predetermined cycle. The clock-recovery symbol includes clock edges for detecting timings at which data change. In general, 8b/10b, a Manchester-encoded signal, and the like are known as the reception data SYSDATA.

Figure 4:
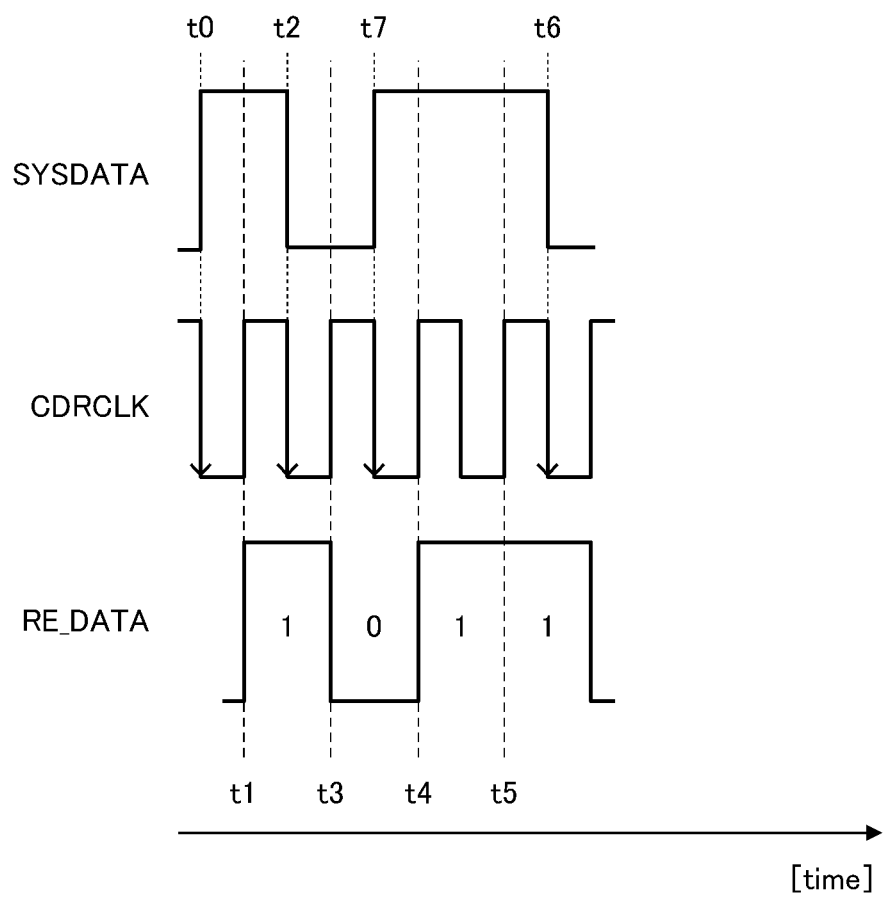
FIG. 4 is a timing chart showing a logical state of a major node of the imager-clock generation unit IMG_CLK shown in FIG. 2.

The clock-data recovery unit CDR executes phase adjustment so that the phase of the reception data SYSDATA matches the phase of a falling clock of the CDR clock CDRCLK (see lines at time points t2 and t6 in FIG. 4).

A phase-and-frequency comparator PD in the clock-data recovery unit CDR samples a value of the reception data SYSDATA at timings of rising edges of the CDR clock CDRCLK (see lines at time points t1, t3, t4, and t5 in FIG. 4) and outputs re-timing data RE_DATA synchronized with the CDR clock CDRCLK to the register unit REG.

The data held in the register unit REG is used for setting an operation mode or the like in the camera unit 2.

The phase-and-frequency comparator PD further compares a falling timing (see lines at time points t0, t2, t7, and t6 in FIG. 4) of the CDR clock CDRCLK with a tuning of generating an edge of the reception data SYSDATA at the falling timing of the CDR clock CDRCLK. When the phase-and-frequency comparator PD determines that the phase of the CDR clock CDRCLK is behind the phase of the reception data SYSDATA, the output from an UP terminal of the phase-and-frequency comparator PD becomes H and a current is supplied from a charge pump CP in the clock-data recovery unit CDR to a loop filter LF in the clock-data recovery unit CDR.

Consequently, the voltage in the loop filter LF gradually increases and the oscillation frequency of a voltage-controlled oscillator VCO_CDR in the clock-data recovery unit CDR increases.

When the phase-and-frequency comparator PD compares the falling timing of the CDR clock CDRCLK with the timing of generating the edge of the reception data SYSDATA and determines that the phase of the CDR clock CDRCLK is ahead of the phase of the reception data SYSDATA, the output from a DOWN terminal of the phase-and-frequency comparator PD becomes H and the electric charge accumulated in the loop filter LF is extracted by the charge pump CP.

Consequently, the voltage in the loop filter LF gradually decreases and the oscillation frequency of the voltage-controlled oscillator VCO_CDR decreases.

When the phase of the CDR clock CDRCLK is the same as the clock phase of the reception data SYSDATA, the output of both the UP terminal and the DOWN terminal does not become H. Alternatively, the period in which the UP terminal becomes H matches the period in which the DOWN terminal becomes H in a predetermined period. Therefore, the voltage in the loop filter LF is fixed and the oscillation frequency of the voltage-controlled oscillator VCO_CDR is fixed.

The principle of phase adjustment in the phase-and-frequency comparator PD is described above. Frequency adjustment is performed by using a similar principle.

Here, an operation of switching between communication directions will be described with reference to FIG. 5.

Figure 5:
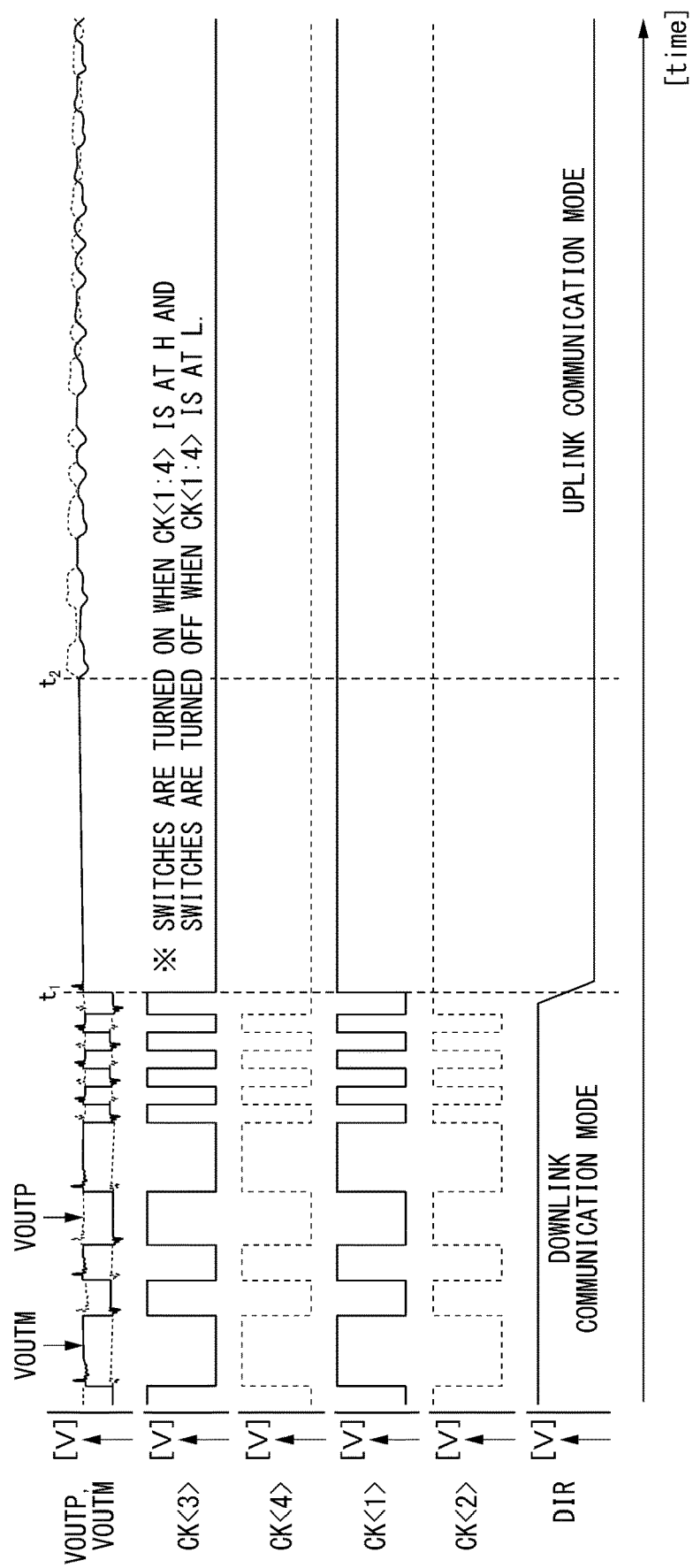
FIG. 5 is a timing chart showing an operation of the imaging system according to a first embodiment of the present invention.

FIG. 5 is a timing chart showing an operation of the imaging system according to the first embodiment of the present invention. Here, FIG. 5 shows results of the simulation of transient response of two-way communication. VOUTP and VOUTM shown in FIG. 5 indicate a differential signal in the pad P1 of the camera unit 2 and a differential signal in the pad M1 of the camera unit 2, respectively.

As shown in FIG. 5, in a period of downlink communication, the states of switches SW1 to SW4 included in the output driver Tx1 are intermittently switched between on the basis of clocks CK<1> to CK<4>.

In addition, in a period of uplink communication, the switches SW3 and SW4 are turned off, and the switches SW1 and SW2 are maintained to be turned on and function as a termination resistor of the receiver Rx2. At the same time, the switches SW1 and SW2 have resistance values of approximately 50Ω and form a returning current path for an output driver Tx2 (output driver 306).

When the communication mode is switched from a downlink communication mode to an uplink communication mode shown in FIG. 5 at a time point t1, switching of VOUTP and VOUTM is stopped. Here, in FIG. 5, communication directions are controlled on the basis of DIR in order to simplify the description. In fact, data for reporting completion of data communication are included at the end of each of an uplink signal and a downlink signal, and actual communication directions change when the information-processing unit 3 or the camera unit 2 receives the data. Details of this will be described later with reference to FIG. 4.

Transmission of a signal from the output driver Tx2 is started at the time point t1 and the signal at this node is stable until a time point t2 at which the signal reaches the receiver Rx2. When the signal from the output driver Tx2 reaches the receiver Rx2 at the time point t2, switching waveforms appear again in a VOUTP terminal and a VOUTM terminal. The VOUTP terminal and the VOUTM terminal are indicated by the pad P1 and the pad M1 in FIG. 2, respectively.

As shown in FIG. 4, a system-line completion command (for example, "1011") is transmitted from the information-processing unit 3 and this value is detected as the re-timing data RE_DATA. At this time, the communication mode is changed to the downlink communication mode (time points 0 to t1 in FIG. 5) and the camera unit 2 outputs a digital video signal (imaging data PIX_DATA) to the information-processing unit 3.

When the downlink communication mode is started, a switch SW shown in FIG. 3 is turned off and the voltage in the loop filter LF is maintained. Therefore, the voltage supplied to the voltage-controlled oscillator VCO_CDR in the period of the downlink communication mode is fixed and the frequency of the CDR clock CDRCLK in the period is fixed.

The camera unit 2 outputs an imager-line completion command to the system after outputting a digital video signal (imaging data PIX_DATA) of one line to the information-processing unit 3. Thereafter, the communication mode is changed to the uplink communication mode again.

In the uplink communication mode, the switch SW is short-circuited again and an operation of frequency lock (re-adjustment) of the CDR clock CDRCLK and an operation of extracting the reception data SYSDATA are executed on the basis of the reception data SYSDATA.

A configuration of the information-processing unit 3 will be described with reference to FIG. 2.

<Configuration of Information-Processing Unit 3>

The information-processing unit 3 includes the receiver 301, a clock-data recovery unit 302, a reception-signal-processing unit 303 (reception-key generation unit or processing circuit), a crystal oscillator 304, an uplink-signal generation unit 305, and the output driver 306. The receiver 301 is shown as a differential-signal reception unit Rx1. Hereinafter, the receiver 301 is called a receiver Rx1 (second transmission circuit). The clock-data recovery unit 302 is shown as CDR_SYS. The crystal oscillator 304 is abbreviated as Xtal. The output driver 306 is shown as a differential-signal transmission unit Tx2. Hereinafter, the output driver 306 is called an output driver Tx2.

The receiver Rx1 is a circuit to binarize imaging data (downlink packet) including pixel data received as a differential amplified signal in the pad P2 and the pad M2.

The clock-data recovery unit 302 receives the imaging data (downlink packet) including the pixel data and outputs the imaging data to the reception-signal-processing unit 303 as data RE_DATA_SYS. The data RE_DATA_SYS are captured by the reception-signal-processing unit 303 at a timing synchronized with a signal CDRCLK_SYS. The reception-signal-processing unit 303 executes image-processing on the data RE_DATA_SYS. This processing includes processing of converting the imaging data on which gradation correction or the like has been performed into a format that the display 4 is able to display.

The configuration of the clock-data recovery unit 302 is the same as that of the clock-data recovery unit 206a in the above-described camera unit 2. The data RE_DATA_SYS shown in FIG. 2 constitute a digital signal indicating the imaging data transmitted from the image sensor (camera unit 2). The signal CDRCLK_SYS is a basic clock signal generated by using a clock-recovery symbol included in the downlink packet.

The reception-signal-processing unit 303 captures the data RE_DATA_SYS at a timing synchronized with the signal CDRCLK_SYS and displays the data RE_DATA_SYS on the display 4 after predetermined signal-processing is performed on the data RE_DATA_SYS.

The crystal oscillator 304 (a quartz-crystal unit or a crystal unit) is an element used for generating oscillation with high accuracy in frequency by using the piezoelectric effect of crystal (quartz) and outputs a system clock SYS_CLK.

In addition, the reception-signal-processing unit 303 compares the frequency of the signal CDRCLK_SYS and the frequency of the system clock SYS_CLK. When the frequency of the signal CDRCLK_SYS is higher than the frequency of the system clock SYS_CLK, the reception-signal-processing unit 303 outputs a command for reducing the frequency of the clock generated by the imager-clock generation unit IMG_CLK in the camera unit 2 to the uplink-signal generation unit 305. On the other hand, when the frequency of the signal CDRCLK_SYS is lower than the frequency of the system clock SYS_CLK, the reception-signal-processing unit 303 outputs a command for increasing the frequency of the clock generated by the imager-clock generation unit IMG_CLK in the camera unit 2 to the uplink-signal generation unit 305.

In other words, the reception-signal-processing unit 303 continues to output a feedback command (register-setting information) to the uplink-signal generation unit 305 so that the frequency of the imager clock IMCLK matches the system clock SYS_CLK.

In addition, the reception-signal-processing unit 303 recognizes predetermined partial data in the received imaging data as the transmission key, generates the reception key on the basis of the transmission key, and outputs the reception key to the uplink-signal generation unit 305.

The uplink-signal generation unit 305 generates the uplink packet including the reception key generated by the reception-signal-processing unit 303 and the register-setting information constituting the register-setting signal indicating an imaging condition of the imager, thus generating an uplink packet.

The output driver Tx2 transmits the uplink packet generated by the uplink-signal generation unit 305 to the receiver 204 in the camera unit 2.

Here, the reception key generated by the reception-signal-processing unit 303 is the same data as the transmission key transmitted by the camera unit 2. In other words, the camera unit 2 determines that a transmission error caused by disturbance noise or the like has not occurred only when the reception key and the transmission key match each other in both the period of transmission by the camera unit 2 and the period of reception by the camera unit 2. In the period of transmission by the camera unit 2, the camera unit 2 transmits the transmission key and the information-processing unit 3 receives the transmission key. In the period of reception by the camera unit 2, the information-processing unit 3 transmits the reception key and the camera unit 2 receives the reception key. The same data mean that, for example, the reception key may be "1110" acquired by inverting the transmission key of "0001." Therefore, the predetermined condition used when the camera unit 2 collates the reception key generated on the basis of the transmission key by the information-processing unit 3 with the transmission key is a condition including the case in which the reception key and the transmission key completely match each other. The predetermined condition may be looser than the above-described condition and may indicate that disturbance noise has not occurred.

In addition, when the transmission key and the reception key meet the predetermined condition, the camera unit 2 writes in the register unit 206b the register-setting information (register-setting signal) that is transmitted along with the reception key and is last received. If a transmission error does not occur, the reception key is the same as the transmission key. In other words, the camera unit 2 updates the register unit 206b. By updating the register unit 206b, the voltage value output by the digital-to-analog convertor 206c (on-chip DAC) is changed and the deviation in frequency between the imager clock IMCLK and the system clock SYS_CLK becomes small.

In this way, the register unit 206b is updated with a new value of the register-setting information only when the reception key and the transmission key match each other and therefore it is possible to provide the camera unit 2 (image sensor) that is small and is able to operate stably even when disturbance noise is generated by an electric scalpel or the like.

In addition, by using the first pad (the pad P1 and the pad M1) included in the camera unit 2, the camera unit 2 receives the uplink packet including the register-setting signal transmitted from the second pad (the pad P2 and the pad M2) included in the information-processing unit 3. These pads are connected to each other by the signal transmission line (the cable CABLEP and the cable CABLEM). Therefore, a signal line such as a dedicated line for the register-setting signal other than the signal transmission line is unnecessary in order to transmit the register-setting signal.

The transmission key is configured as the predetermined partial data in the imaging data, but it may be imaging data of which pixel positions are designated in advance. In such a case, it is possible to share the imaging data and the transmission key and therefore it is also possible to provide a robust image sensor for disturbance noise without increasing the amount of communication of the downlink packets. The case in which the transmission key is configured as the imaging data of which pixel positions are designated in advance will be described in the following second embodiment.

Second Embodiment

Next, a second embodiment will be described with reference to FIG. 6 and FIG. 7.

Figure 6:
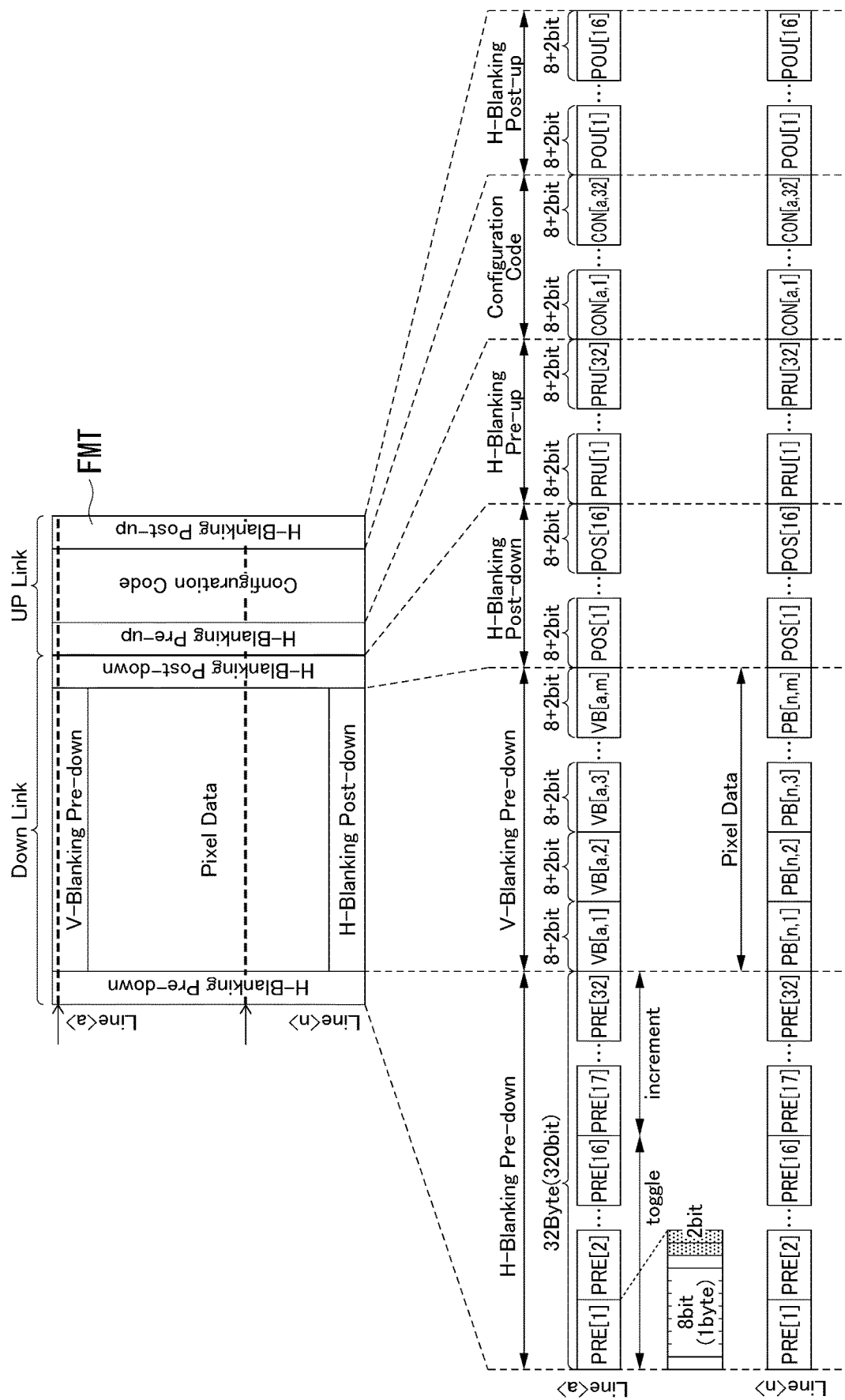
FIG. 6 is a diagram showing an example of a configuration of a format of an image transmitted and received by a camera unit according to a second embodiment of the present invention.

FIG. 6 is a diagram showing an example of a configuration of a format of an image transmitted and received by a camera unit of the present invention. In addition, FIG. 7 is a flow chart showing an operation of the camera unit of the present invention.

In FIG. 6, a frame-format structure FMT of the camera unit 2 (image sensor) is shown on the upper side.

The frame-format structure FMT is mostly divided into a downlink period in which data (downlink packets) are transmitted in the direction from the camera unit 2 to the information-processing unit 3 and an uplink period in which data (uplink packets) are transmitted in the direction from the information-processing unit 3 to the camera unit 2.

The frame-format structure in the downlink period includes a horizontal pre-blanking section H-Blanking Pre-down, a horizontal post-blanking section H-Blanking Post-down, a vertical pre-blanking section V-Blanking Pre-down, a vertical post-blanking section V-Blanking Post-down, and a pixel-data section Pixel Data.

The frame-format structure in the uplink period includes a horizontal pre-blanking section H-Blanking Pre-up, a horizontal post-blanking section H-Blanking Post-up, and a control-code section Configuration Code.

Hereinafter, a data configuration of the line (Line <a>) including the vertical pre-blanking section V-Blanking Pre-down will be described by using data shown on the lower side of FIG. 6.

The Line <a> includes the horizontal pre-blanking section H-Blanking Pre-down, the vertical pre-blanking section V-Blanking Pre-down, the horizontal post-blanking section H-Blanking Post-down, the horizontal pre-blanking section H-Blanking Pre-up, the control-code section Configuration Code, and the horizontal post-blanking section H-Blanking Post-up.

All the data constituting the frame-format structure FMT are modulated by using 8b/10b modulation. Since the 8b/10b modulation uses a data configuration in which clock-recovery symbols of two bits are added to data of one byte (eight bits), information of ten bits is necessary for expressing information of one byte.

Data conversion from 8b to 10b is performed in accordance with a conversion table known as a K code or a D code.

The horizontal pre-blanking section H-Blanking Pre-down includes a region having the length of 320 bits of which the data amount is 32 bytes.

As a data configuration of the line direction, a preamble period Preamble is necessary for the information-processing unit 3 to lock the data output from the imager.

The former half, which has 160 bits (16 bytes), of the preamble period Preamble includes a toggle signal repeatedly having "010101 . . . " and the latter half, which has 160 bits (16 bytes), of the preamble period Preamble includes an increment signal having "0x00," "0x01," . . . , "0x 0f."

The toggle signal is used as data necessary for the clock-data recovery unit CDR_SYS to take out data by detecting clock-recovery symbols that follow the toggle signal and are included in the data modulated by using the 8b/10b modulation. The clock-data recovery unit CDR_SYS performs a pull-in operation for operating at the same frequency and phase as those of the imager clock IMCLK by using the toggle signal.

Since the pull-in operation of a frequency and a phase is performed by using clock edges of the digital signal generated on the basis of the imager clock IMCLK, the toggle signal having the greatest number of changes of the clock per unit time is the most suitable.

The latter half of the increment signal is used for detecting the head position of data.

In the communication method proposed in the embodiment, it is difficult to detect the head position of data. Therefore, by searching for the boundary position of data so that the increment signal following the toggle signal is correctly detected, the system (information-processing unit 3) can read information inside the image sensor (camera unit 2). The information is included in the vertical pre-blanking section V-Blanking Pre-down or the vertical post-blanking section V-Blanking Post-down following the horizontal pre-blanking section H-Blanking Pre-down.

The information included in the vertical pre-blanking section V-Blanking Pre-down or the vertical post-blanking section V-Blanking Post-down may include temperature information and voltage information inside the image sensor or may include pull-in data (for example, a toggle signal) in order for the system to perform frequency-and-phase pull-in on the signal output from the imager.

When the vertical pre-blanking section V-Blanking Pre-down or the vertical post-blanking section V-Blanking Post-down is completed, the horizontal post-blanking section H-Blanking Post-down is started.

A line-completion code EOL, which indicates that data transmission of the line is completed, is included in the horizontal post-blanking section H-Blanking Post-down. When the line-completion code EOL reaches the system (information-processing unit 3), the uplink period in which data transmission from the system (information-processing unit 3) to the imager (camera unit 2) is performed is started.

The data configuration and the purpose of the horizontal pre-blanking section H-Blanking Pre-up and the horizontal post-blanking section H-Blanking Post-up in the uplink period are the same as those of the horizontal pre-blanking section H-Blanking Pre-down and the horizontal post-blanking section H-Blanking Post-down. Therefore, details of them will not be described.

The only difference is the direction of data communication.

The control-code section Configuration Code includes resister information for determining the setting of the image sensor (camera unit 2).

The resister information is temporarily stored on the register unit REG (register unit 206b). The resister information is used as a valid register value only when the collation circuit COLL (collation circuit 202a) determines that the information is correct. Only the valid register value is used for setting the output voltage of the DA convertor DAC (digital-to-analog convertor 206c) and the operation mode of the timing generator TG (TG 207). According to the image sensor in the embodiment, setting values are not changed to new values unless the collation circuit COLL determines that the resister information is correct even when signals are transmitted under the environment where disturbance noise is generated by an electric scalpel or the like. Therefore, it is possible to provide the robust image sensor (camera unit 2) and imaging system 1 for disturbance noise.

The line <n> includes the horizontal pre-blanking section H-Blanking Pre-down, the pixel-data section Pixel Data, the horizontal post-blanking section H-Blanking Post-down, the horizontal pre-blanking section H-Blanking Pre-up, the control-code section Configuration Code, and the horizontal post-blanking section H-Blanking Post-up.

The difference from the Line <a> is only the pixel-data section Pixel Data. Hereinafter, only the pixel-data section Pixel Data will be described.

The pixel-data section Pixel Data includes pixel element data P[n, m]. The pixel element data P[n, m] include element data of ten bits including imaging data information of eight bits and embedded clock information of two bits. Transmission and reception of the pixel element data P[n, m] are processed in accordance with a similar operation principle to that of transmission and reception of the control-code section Configuration Code.

In a case in which imaging data having the bit length (for example, ten bits) greater than eight bits need to be transmitted, it is also possible to incorporate information of two bits, which have not been transmitted, for each of four pixels into a unit so as to generate new pixel element data Pex[n/4, m/4]. It is possible to execute transmission and reception of the pixel element data Pex[n/4, m/4].

Here, the camera unit 2 transmits the imaging data including the pixel data to the information-processing unit 3 as the downlink packet and the information-processing unit 3 receives the downlink packet, recognizes predetermined partial data in the imaging data as the transmission key, and generates the reception key on the basis of the transmission key, as described in the first embodiment.

In the second embodiment, the position of the transmission key in the imaging data will be described below in order to clarify the description "the transmission key may be imaging data of which pixel positions are designated in advance."

The transmission key may be included in the imaging data and may be configured as information indicating pixel data of a predetermined pixel. Here, the predetermined pixel indicates a pixel designated in advance in the above-described pixel-data section Pixel Data.

In addition, the transmission key may be configured as information indicating the uppermost bit of a predetermined pixel in the pixel data of the imaging data.

Here, the information indicating the uppermost bit corresponds to information indicating a bit that is the most influential in brightness compared to information indicating the lowermost bit. Therefore, in a case in which transmission data constitute information of p bits, the information indicating the uppermost bit of the predetermined pixel is information indicating the uppermost bit of p bits. In the embodiment, p is eight.

In addition, the imaging data may include the pixel data and service data for controlling start and completion of transmission of the pixel data. The transmission key may be part of the service data.

Here, the service data for controlling start and completion of transmission of the pixel data indicate the horizontal pre-blanking section H-Blanking Pre-down and the horizontal post-blanking section H-Blanking Post-down described above. In addition, the transmission key indicates part of the increment signal following the toggle signal or indicates a signal including part of the service data, that is, the line-completion code EOL in the horizontal post-blanking section H-Blanking Post-down.

In a case in which the transmission key is the pixel data, the pixel data of a predetermined pixel position needs to be updated and held by the collation circuit (holding circuit) each time the downlink packet is transmitted. On the other hand, the service data are output from the imager 201 as fixed data. Therefore, in a case in which the transmission key is part of the service data, the operation is unnecessary in which the transmission key is updated and held by the collation circuit each time the downlink packet is transmitted. A holding circuit other than the collation circuit 202a may hold the transmission key.

When the transmission key and the reception key do not meet a predetermined condition, the collation circuit 202a transmits a downlink packet including an error signal indicating an error position of the transmission key to the information-processing unit 3. The information-processing unit 3 executes an interpolation operation on the pixel corresponding to the error position of the transmission key. The error position indicates the position of the transmission key at which the error has occurred.

Here, executing the above-described interpolation operation on the pixel corresponding to the error position of the transmission key means executing an arithmetic operation on the basis of the imaging data of the same pixel from a previous frame as the pixel corresponding to the error position or on the basis of an average value of the imaging data of pixels around the pixel corresponding to the error position. For example, the pixels around the pixel corresponding to the error position are four pixels around the pixel.

Next, an operation of the camera unit 2 will be described with reference to FIG. 7.

Figure 7:
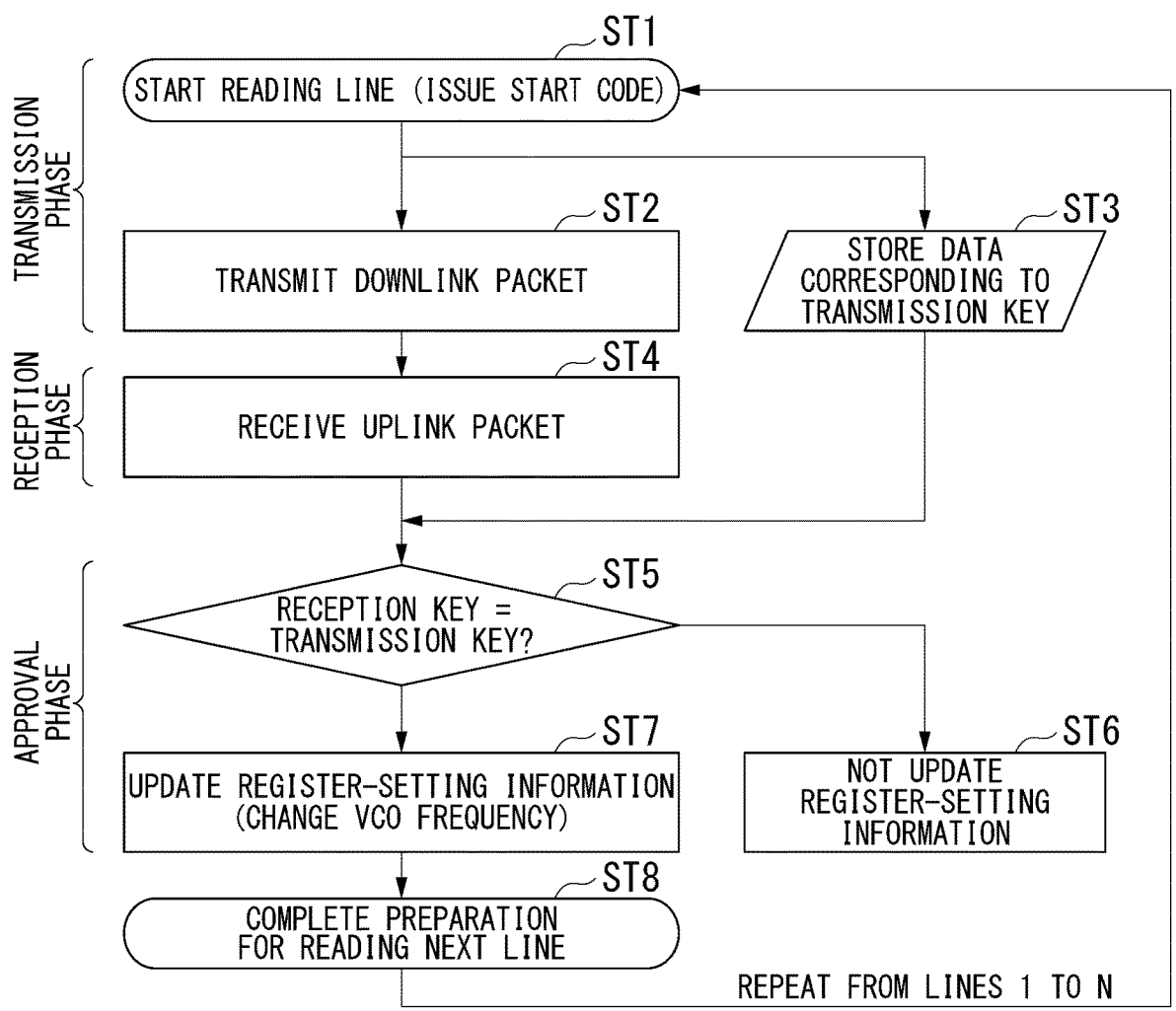
FIG. 7 is a flow chart showing an operation of the camera unit according to the second embodiment of the present invention.

The "transmission phase" in FIG. 7 indicates a state in which the camera unit 2 transmits a downlink packet to the information-processing unit 3. The "reception phase" indicates a state in which the camera unit 2 receives an uplink packet from the information-processing unit 3. The "approval phase" indicates a state in which the value of the register unit 206b is updated with the register-setting information.

The camera unit 2 starts reading a line of a downlink packet to be transmitted (Step ST1). Specifically, the camera unit 2 reads a start code Start Code included in the horizontal pre-blanking section H-Blanking Pre-down corresponding to the Line <1> in the frame format FMT and prepares for transmission of data (downlink packet) having the frame-format structure in the downlink period of the Line <1> in the frame format FMT.

The camera unit 2 executes transmission of the downlink packet (Step ST2). Specifically, the camera unit 2 transmits data having the frame-format structure in the downlink period of the Line <1> in the frame format FMT to the information-processing unit 3. This downlink packet may include correct/incorrect information related to the results of collating the reception encryption key with the transmission encryption key of the line that is one or more lines before the Line <1>. Details of the correct/incorrect information will be described when the following Step ST5 and Step ST6 are described.

The camera unit 2 stores data corresponding to the transmission encryption key (transmission key) included in the downlink packet (Step ST3). Specifically, when the Line <1> includes data corresponding to the transmission encryption key (transmission key) included in the downlink packet, the downlink-signal-processing unit 202 in the camera unit 2 stores the data on a built-in memory (not shown in the drawing) of the downlink-signal-processing unit 202, on the collation circuit COLL, or on the register unit 206*b*.

The camera unit 2 receives an uplink packet (Step ST4). Specifically, the camera unit 2 receives data having the frame-format structure in the uplink period of the Line <1> in the frame format FMT from the information-processing unit 3. The data include the register-setting information and the reception key generated on the basis of the transmission key by the information-processing unit 3 as the control-code section Configuration Code.

The camera unit 2 determines whether or not the reception key and the transmission key match each other (Step ST5). Specifically, the collation circuit 202*a* in the camera unit 2 determines whether or not the stored transmission key and the reception key transmitted from the information-processing unit 3 meet the above-described predetermined condition.

When the stored transmission key and the reception key transmitted from the information-processing unit 3 do not meet the above-described predetermined condition (Step ST5—NO), the camera unit 2 does not update the register-setting information. In addition, the result of the determination is stored inside the camera unit 2 as the correct/incorrect information (Step ST6).

On the other hand, when the stored transmission key and the reception key transmitted from the information-processing unit 3 meet the above-described predetermined condition (Step ST5—YES), the camera unit 2 updates the register-setting information (Step ST7). Specifically, the collation circuit 202*a* updates the register-setting information in the register unit 206*b*. In addition, the digital-to-analog convertor 206*c* changes the voltage value to be output, thus reducing the deviation in frequency between the imager clock IMCLK and the system clock SYS_CLK. Moreover, the result of determining whether or not the above-described predetermined condition is met is stored inside the camera unit 2 as the correct/incorrect information.

After preparation of reading the next line is completed, the processing executed by the camera unit 2 returns to Step ST1 (Step ST8). Specifically, the camera unit 2 makes preparations for reading the next Line <2>. After the preparations are made, the processing returns to Step ST1.

The processing of Steps ST1 to ST9 is repeatedly executed from the Line <1> to the Line <N>. When the processing of Step ST8 of the Line <N> is completed, the processing of one frame is completed.

In this series of processing, the correct/incorrect information received by the information-processing unit 3 has an influence on the contents of uplink packets transmitted by the information-processing unit 3 in the next line.

When the correct/incorrect information received by the information-processing unit 3 in the present line indicates that the update of the register-setting information in the camera unit 2 has failed, programing (updating) data of the register value for the address at which the update of the register value has failed is transmitted again in the next line.

When the correct/incorrect information received by the information-processing unit 3 in the present line indicates that the update of the register-setting information in the camera unit 2 has been successful, data for the update of the register value at a different address from that updated in the present line are transmitted in the next line.

The transmission key may be imaging data of which pixel positions are designated in advance. In such a case, it is possible to share the imaging data and the transmission key and therefore it is also possible to provide a robust image sensor for disturbance noise without increasing the amount of communication of the downlink packets.

In addition, the information-processing unit 3 can find out the address of the register inside the camera unit 2 at which the update of the register value has failed by receiving the correct/incorrect information. Therefore, the information-processing unit 3 can continue to retransmit data for the address of the register at which the update of the register value has failed until the camera unit 2 succeeds in the update of the register value. In other words, it is possible to provide a robust imaging system for disturbance noise.

Third Embodiment

Next, a third embodiment will be described with reference to FIG. 2.

In the description of the imaging system 1 shown in FIG. 2, the camera unit 2 and the information-processing unit 3 are described as a generic concept in the first and second embodiments. Here, the camera unit 2 and the information-processing unit 3 are described as a specific concept.

The camera unit 2 further includes a voltage-controlled oscillator 206*d* (oscillator) that generates an imager clock that is a reference of operation timings of the imager 201. The camera unit 2 generates a signal as a downlink packet by superimposing the imager clock IMCLK on the imaging data and transmits the signal as the downlink packet to the information-processing unit 3.

On the other hand, the information-processing unit 3 further includes a crystal oscillator 304 (system clock generator) and a clock-data recovery unit 302 (clock-data recovery circuit). The crystal oscillator 304 generates the system clock SYS_CLK in the information-processing unit 3. The clock-data recovery unit 302 reproduces the imager clock IMCLK superimposed on the received downlink packet as a basic clock signal CDRCLK_SYS.

The information-processing unit 3 compares the frequency of the imager clock IMCLK with the frequency of the system clock SYS_CLK and transmits the register-setting information (register-setting signal) for reducing the deviation in frequency between the imager clock IMCLK and the system clock SYS_CLK as an uplink packet.

In addition, the voltage-controlled oscillator 206*d* (oscillator) is configured as a voltage-controlled oscillator and the frequency of the imager clock IMCLK is changeable in accordance with the voltage applied to the voltage-controlled oscillator 206*d*. The camera unit 2 further includes a digital-to-analog convertor 206*c* that supplies the voltage to the voltage-controlled oscillator 206*d* on the basis of the frequency that has been set in the register unit 206*b*.

In this way, it is possible to provide an imaging system (endoscope system) that causes the imager clock IMCLK in the camera unit 2 to be a clock synchronized with the system clock SYS_CLK in the information-processing unit 3 by correctly executing a rewriting operation of the register-setting signal without blocking transmission and reception of the imaging data.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging system, comprising:
   a camera unit; and
   an information-processing unit,
   wherein the camera unit and the information-processing unit are configured to communicate with each other in a wired or wireless manner,
   the camera unit comprises:
      an imager configured to generate pixel data;
      a register in which an imaging condition of the imager is to be written;
      a collation circuit;
      a first transmission circuit configured to transmit imaging data including the pixel data to the information-processing unit as a downlink packet;
      a holding circuit configured to hold predetermined data in the imaging data as a transmission key; and
      a writing circuit,
   the information-processing unit comprises:
      a processing circuit configured to receive the downlink packet, recognize the predetermined data in the imaging data as the transmission key, and generate a reception key on the basis of the transmission key; and
      a second transmission circuit configured to transmit an uplink packet including the reception key and a register-setting signal indicating the imaging condition to the camera unit, and
   the writing circuit is configured to write the register-setting signal received with the reception key in the register when the collation circuit collates the transmission key held by the holding circuit with the reception key received from the information-processing unit and the transmission key and the reception key meet a predetermined condition.

2. The imaging system according to claim 1,
   wherein the camera unit comprises a first pad,
   the information-processing unit comprises a second pad connected to the first pad by a signal transmission line, and
   communication of the downlink packet and the uplink packet is performed by using the first pad and the second pad.

3. The imaging system according to claim 1,
   wherein the camera unit is configured to repeat a transmission phase, a reception phase, and an approval phase,
      wherein the first transmission circuit is configured to transmit the downlink packet to the information-processing unit in the transmission phase, the processing circuit is configured to receive the uplink packet from the information-processing unit in the reception phase, and the collation circuit is configured to collate the transmission key with the reception key and determine whether or not the register-setting signal is to be written in the register in the approval phase, and
   the first transmission circuit is configured to transmit, in the transmission phase, information corresponding to a result of collating the transmission key with the reception key to the information-processing unit in the approval phase.

4. The imaging system according to claim 1,
   wherein the transmission key is configured as information indicating the pixel data of a predetermined pixel.

5. The imaging system according to claim 4,
   wherein the transmission key includes information indicating the uppermost bit of the pixel data of the predetermined pixel.

6. The imaging system according to claim 1,
   wherein the first transmission circuit is configured to transmit the downlink packet including an error signal indicating an error position of the transmission key to the information-processing unit when the transmission key and the reception key do not meet the predetermined condition, and
   the information-processing unit is configured to execute an interpolation operation on a pixel corresponding to the error position.

7. The imaging system according to claim 1,
   wherein the imaging data include the pixel data and service data for controlling start and completion of transmission of the pixel data, and
   the transmission key is part of the service data.

8. The imaging system according to claim 1,
   wherein the camera unit further comprises an oscillator configured to generate an imager clock that is a reference of operation timings of the imager,
   the first transmission circuit is configured to generate a signal by superimposing the imager clock on the imaging data and transmit the signal as the downlink packet to the information-processing unit,
   the information-processing unit further comprises:
      a system clock generator configured to generate a system clock in the information-processing unit; and
      a clock-data recovery circuit configured to reproduce the imager clock superimposed on the received downlink packet, and
   the second transmission circuit is configured to compare a frequency of the imager clock with a frequency of the system clock and transmit the register-setting signal for reducing deviation in frequency between the imager clock and the system clock as the uplink packet.

9. The imaging system according to claim 8,
   wherein the oscillator is configured as a voltage-controlled oscillator,
   a frequency of the imager clock is changeable in accordance with a voltage applied to the voltage-controlled oscillator, and
   the camera unit further comprises a digital-to-analog convertor configured to supply a voltage to the voltage-controlled oscillator on the basis of a frequency that has been set in the register.

10. An imaging method in an imaging system including a camera unit and an information-processing unit, the method comprising a first step, a second step, a third step, a fourth step, and a fifth step,
    wherein the camera unit and the information-processing unit are configured to communicate with each other in a wired or wireless manner,
    the camera unit includes:
       an imager configured to generate pixel data;
       a register in which an imaging condition of the imager is to be written;
       a collation circuit;
       a first transmission circuit;
       a holding circuit; and
       a writing circuit,
    the information-processing unit includes:
       a processing circuit; and
       a second transmission circuit, the first transmission circuit transmits imaging data including the pixel data to the information-processing unit as a downlink packet in the first step, the holding circuit holds predetermined data in the imaging data as a transmission key in the second step, the processing circuit receives the downlink packet, recognizes the predetermined data in the imaging data as the transmission key, and generates a reception key on the basis of the transmission key in the third step, the second transmission circuit transmits an uplink packet including the reception key and a register-setting signal indicating the imaging condition to the camera unit in the fourth step, and the writing circuit writes the register-setting signal received with the reception key in the register in the fifth step when the collation circuit collates the transmission key held by the holding circuit with the reception key received from the information-processing unit and the transmission key and the reception key meet a predetermined condition.

\* \* \* \* \*